(12) United States Patent
Van Der Horst et al.

(10) Patent No.: US 11,564,584 B2
(45) Date of Patent: Jan. 31, 2023

(54) SYSTEM FOR DETERMINING BLOOD FLOW

(71) Applicant: KONINKLIJKE PHILIPS N.V., Eindhoven (NL)

(72) Inventors: Arjen Van Der Horst, Tilburg (NL); Anna Hendrika Van Dusschoten, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 798 days.

(21) Appl. No.: 16/336,147

(22) PCT Filed: Sep. 22, 2017

(86) PCT No.: PCT/EP2017/073985
§ 371 (c)(1),
(2) Date: Mar. 25, 2019

(87) PCT Pub. No.: WO2018/060064
PCT Pub. Date: Apr. 5, 2018

(65) Prior Publication Data
US 2019/0239755 A1 Aug. 8, 2019

(30) Foreign Application Priority Data
Sep. 28, 2016 (EP) .................................... 16191062

(51) Int. Cl.
*A61B 5/028* (2006.01)
*A61B 5/01* (2006.01)
(Continued)

(52) U.S. Cl.
CPC .............. *A61B 5/028* (2013.01); *A61B 5/015* (2013.01); *A61B 5/02154* (2013.01);
(Continued)

(58) Field of Classification Search
CPC ..... A61B 5/028; A61B 5/015; A61B 5/02154; A61B 2090/3614; A61B 2562/0266; A61B 2562/0271; A61B 2562/043; A61M 5/007
See application file for complete search history.

(56) References Cited

U.S. PATENT DOCUMENTS 3,545,428 A * 12/1970 Webster, Jr. ........... A61B 5/028
600/505
6,394,961 B1 * 5/2002 Pfeiffer .................. A61B 5/028
600/505
(Continued)

FOREIGN PATENT DOCUMENTS

WO 2001018513 A1 3/2001
WO 2012121584 A1 9/2012
(Continued)

OTHER PUBLICATIONS

Ganz, W. et al., "Measurement of Coronary Sinus Blood Flow by Continuous Thermodilution in Man", Circulation, vol. 44, No. 2, Aug. 1971.
(Continued)

*Primary Examiner* — Sean D Mattson

(57) ABSTRACT

The invention relates to a system for determining blood flow within a blood vessel (18). A fluid infusion unit (4, 10, 11) continuously infuses a fluid into the blood vessel, and a temperature values determining unit (14, 21) determines simultaneously a first temperature value at a first location and a second temperature value at a second location such that the first temperature value is indicative of the temperature of the fluid and the second temperature value is indicative of the temperature of a mixture of the fluid and the blood. The blood flow is determined based on the measured first and second temperature values and the infusion rate. This kind of determining the blood flow leads to an
(Continued)

increased accuracy and is less cumbersome than known techniques requiring a movement of a temperature sensor for measuring temperatures at different locations.

10 Claims, 3 Drawing Sheets

(51) Int. Cl.
*A61B 5/0215* (2006.01)
*A61M 5/00* (2006.01)
A61B 90/00 (2016.01)

(52) U.S. Cl.
CPC ..... *A61M 5/007* (2013.01); *A61B 2090/3614* (2016.02); *A61B 2562/0266* (2013.01); *A61B 2562/0271* (2013.01); *A61B 2562/043* (2013.01)

(56) References Cited

U.S. PATENT DOCUMENTS

| | | | |
|---|---|---|---|
| 7,775,988 B2 | 8/2010 | Pijls | |
| 2002/0177783 A1* | 11/2002 | Khalil | A61B 5/028 600/505 |
| 2004/0052493 A1 | 3/2004 | Lavoie | |
| 2004/0054293 A1* | 3/2004 | Krivitski | A61B 5/6855 600/505 |
| 2007/0078352 A1* | 4/2007 | Pijls | A61B 5/028 600/504 |
| 2011/0238020 A1* | 9/2011 | Goedje | A61B 5/02154 604/272 |
| 2013/0039384 A1 | 2/2013 | Jester et al. | |
| 2013/0194757 A1 | 8/2013 | Harshbarger | |
| 2014/0194757 A1* | 7/2014 | 'T Hooft | G01F 1/6884 600/505 |
| 2014/0206988 A1* | 7/2014 | Ramachandran | A61B 5/015 600/424 |
| 2014/0323887 A1* | 10/2014 | Anderson | A61B 5/028 600/505 |
| 2015/0335231 A1 | 11/2015 | Van Der Mark et al. | |

FOREIGN PATENT DOCUMENTS

| | | | | |
|---|---|---|---|---|
| WO | 2012164481 A1 | 12/2012 | | |
| WO | 2014072891 A1 | 5/2014 | | |
| WO | WO-2014072891 A1 * | 5/2014 | ............ | A61B 5/036 |
| WO | 2016070099 A1 | 5/2016 | | |

OTHER PUBLICATIONS

Van't Veer, M. et al., "Continuous infusion thermodilution for assessment of coronary flow: Theoretical background and in vitro validation", Medical Engineering & Physics 31 (2009) 688-694.

Kreger, S. et al., "High Resolution Distributed Strain or Temperature Measurements in Single- and Multi-mode Fiber Using Swept-Wavelength Interferometry", Luna Technologies, Blacksburg, VA, 2006.

Kem, M. et al., "Physiological Assessment of Coronary Artery Disease in the Cardiac Catheterization Laboratory", Circulation, 114;1321-1341, 2006.

White C.W., "Clinical applications of Doppler coronary flow reserve measurements". Am. J. Cardiol, 71; 10D-16D, 1993.

Siebes M., et al., "Single-wire pressure and flow velocity measurement to quantify coronary stenosis hemodynamics and effects of percutaneous interventions". Circulation, 109:756-762, 2004.

Leather, H.A. et al. "Evaluation of a new continuous cardiac output monitor in off-pump coronary artery surgery". Anaesthesia, 59;385-389, 2004.

Van der Horst, A. et al., "Thermal anemometric assessment of coronary flow reserve with a pressure-sensing guide wire: an in vitro evaluation" Med Eng Phys, 33; 684 691, 2011.

De Bruyne, et al., "Coronary thermodilution to assess flow reserve—experimental validation". Circulation, 104; 2003-2006, 2001.

Pijls, N.H.J., et al., "Coronary thermodilution to assess flow reserve: Validation in humans". Circulation, 105; 2482-2486, 2002.

Aarnoudse, W.H. et al., "Direct volumetric blood flow measurement in coronary arteries by thermodilution". J Am Coll Cardiol, 50; 2294-2304, 2007.

* cited by examiner

SYSTEM FOR DETERMINING BLOOD FLOW

CROSS-REFERENCE TO PRIOR APPLICATIONS

This application is the U.S. National Phase application under 35 U.S.C. § 371 of International Application No. PCT/EP2017/073985, filed on 22 Sep. 2017, which claims the benefit of European Patent Application No. 16191062.5, filed on 28 Sep. 2016. These applications are hereby incorporated by reference herein.

FIELD OF THE INVENTION

The invention relates to a system, method and computer program for determining blood flow within a blood vessel.

BACKGROUND OF THE INVENTION

The article "Measurement of Coronary Sinus Blood Flow by Continuous Thermodilution in Man" by W. Ganz et al., Circulation, American Heart Association, volume 44, pages 181 to 195 (1971) discloses a continuous thermodilution technique for determining coronary sinus blood flow, wherein a fluid is continuously injected into a blood vessel, wherein the temperatures of i) the blood, ii) the injected fluid and iii) the mixture of the blood and the fluid are measured and wherein these temperatures are used for determining the blood flow.

US 2004/0054293 A1 discloses a catheter comprising an elongate catheter body having a distal end and a proximal end, wherein the elongate catheter body includes an indicator lumen and an insulating lumen and wherein the indicator lumen has a restricted cross-sectional area adjacent the distal end of the elongate catheter body. The catheter further comprises a dilution sensor connected to the elongate catheter body and a guidewire extending through the restricted cross sectional area of the indicator lumen to project from the distal end of the elongate catheter body.

The article "Continuous infusion thermodilution for assessment of coronary flow: Theoretical background and in vitro validation" by M. van't Veer et al., Medical Engineering & Physics, volume 31, pages 688 to 694 (2009) discloses a continuous infusion thermodilution technique for determining intravascular blood flow. An indicator fluid having a relatively cold temperature, i.e. a temperature being lower than the temperature of the blood, is continuously infused into an artery by using a catheter, thereby generating a mixture of the fluid and the blood. A guidewire with a thermistor at its tip is then used to measure the temperature of this mixture at a certain distance from the catheter, while the fluid is infused into the artery with a constant infusion rate. This constant infusion rate is used together with the temperature of the mixture, the temperature of the blood and the temperature of the indicator fluid for determining the arterial blood flow, i.e. the volumetric flow of the blood within the artery. Thus, this technique allows for a determination of a blood flow, but the accuracy of this determination can be rather low.

SUMMARY OF THE INVENTION

It is an object of the present invention to provide a system, a method and a computer program for more accurately determining blood flow within a blood vessel.

In a first aspect of the present invention a system for determining blood flow within a blood vessel is presented, wherein the system comprises:

a fluid infusion unit for continuously infusing a fluid into the blood vessel with an infusion rate such that a mixture of the fluid and the blood is generated within the blood vessel, a temperature values determining unit for simultaneously measuring several temperature values at several locations along the length of the blood vessel such that a temperature profile along the length of the blood vessel is determined and for determining, based on these measured several temperature values, a first temperature value at a first location along the length of the blood vessel and a second temperature value at a second location along the length of the blood vessel such that the first temperature value is indicative of the temperature of the fluid and the second temperature value is indicative of the temperature of the mixture, a blood flow determining unit for determining the blood flow based on the determined first and second temperature values and the infusion rate.

The continuous infusion thermodilution technique disclosed in the above mentioned article by M. van't Veer et al. requires a measurement of different temperatures, i.e. of the temperature of the blood, the temperature of the fluid and the temperature of the mixture, by using the thermistor at the tip of the guidewire. This requires a movement of the guidewire such that its tip is arranged at the different locations along the length of the blood vessel at which the different temperatures can be measured. These temperatures can therefore not be measured simultaneously such that, if something has changed between the times of measuring the different temperatures, these temperatures do not correspond to each other which finally leads to an inaccurate determination of the blood flow. Moreover, the required movement of the guidewire within the blood flow renders this technique relatively cumbersome for a user like a physician carrying out this technique.

In contrast, according to the present invention the first temperature value being indicative of the temperature of the fluid and the second temperature value being indicative of the temperature of the mixture are determined based on the simultaneously measured temperature values forming the temperature profile. It can therefore be ensured that they correspond to each other, i.e. that they have been determined under the same conditions, thereby allowing for an improved accuracy of determining the blood flow within the blood vessel. Moreover, since it is not required to move a guidewire for determining the different temperature values, the procedure can be less cumbersome for the user.

The first and second temperature values can be absolute temperature values being indicative of the absolute temperatures of the fluid and the mixture, or they can be relative temperature values being indicative of relative temperatures of the fluid and the mixture. In the latter case the relative temperatures are preferentially temperatures being relative to the temperature of the blood.

Preferentially, the temperature values determining unit comprises an optical fiber being adapted for measuring the several temperature values at the several locations along the length of the blood vessel. In particular, the temperature values determining unit can be adapted to use swept-wavelength interferometry together with the optical fiber for measuring the several temperature values forming the temperature profile. The optical fiber can be, for instance, a standard optical glass fiber, an optical fiber with an inscribed Bragg grating pattern, or another kind of optical fiber. This allows for a very accurate simultaneous measurement of the temperature values forming the temperature profile, which in turn can lead to a further improved accuracy of determining the blood flow.

The optical fiber can be adapted to also allow for a determination of the different locations along the length of the blood vessel by optical shape sensing. In particular, the optical fiber can be an optical shape sensing fiber which allows for a determination of the locations by optical shape sensing. The system can further comprise a locations determination unit for being connected to the optical fiber for determining the first and second locations, for which the first and second temperature values are determined, by optical shape sensing. This can allow for an accurate arrangement of the optical fiber within a desired part of the blood vessel, without necessarily requiring further tracking techniques for tracking the optical fiber within the blood vessel like a fluoroscopy tracking technique. This can further simplify the handling of the system. The temperature values determining unit and the locations determination unit can be an integrated unit being adapted to perform at least the two tasks of determining the temperature values and the locations, or they can be separate units.

Preferentially, the fluid infusion unit comprises a tube and the system further comprises a longish guiding element like a guidewire for guiding the tube into the blood vessel, wherein the optical fiber is integrated with the guiding element. The same element, i.e. the guiding element, can therefore be used for at least two different purposes, i.e. for guiding the tube, which is preferentially a catheter, into the blood vessel and for arranging the optical fiber within the blood vessel for determining the different temperature values at the different locations along the length of the blood vessel. This allows for a further simplified handling of the system.

The optical fiber can be arranged along a longitudinal axis of the guiding element or wound around the guiding element. The optical fiber can be arranged at the outside of the guiding element, in order to enhance the thermal contact between the optical fiber and the surrounding of which the temperature values need to be determined. However, the optical fiber can also be arranged within the guiding element. The optical fiber can be integrated with the guiding element by arranging it in a slit. If the optical fiber is wound around the guiding element, the optical fiber can also be used to obtain information about a temperature distribution along the perimeter of the guiding element.

The system can further comprise a sensor for generating a sensing signal depending on a property to be sensed within the blood vessel and a power generation unit for powering the sensor by using light received from the optical fiber, wherein the optical fiber can be adapted to transmit the sensing signal to the outside of the blood vessel. Thus, additional information can be provided by using relatively compact equipment, i.e. equipment to be introduced into the blood vessel having a relatively small diameter, because it is not necessarily required to introduce further elements into the blood vessel for powering the sensor and for transmitting the sensor signal to the outside of the blood vessel, in particular to the outside of a patient. In an embodiment the optical fiber is integrated with the guiding element for guiding the tube into the blood vessel, wherein the sensor is arranged at the tip of the guiding element and hence of the optical fiber.

The sensor can be adapted to generate a pressure sensing signal being indicative of the pressure in the blood, wherein the system can further comprise a resistance determination unit for determining the resistance based on the pressure indicated by the pressure sensing signal and the determined blood flow. This allows for an additional interrogation of a disease of the blood vessel indicated by a resistance being outside of a resistance range which is expected for a healthy blood vessel. In particular, this allows for an interrogation of a coronary microvascular disease. The resistance determination unit can be integrated with at least one of the temperature values determining unit and the locations determination unit, or it can be a separate unit.

The first location along the length of the blood vessel can refer to a point location along the length of the blood vessel or can refer to a section of the blood vessel, i.e. the first location can cover a section of the blood vessel. Correspondingly, the second location along the length of the blood vessel can refer to a point location along the length of the blood vessel or can refer to a section of the blood vessel, i.e. also the second location can cover a section of the blood vessel.

The temperature values determining unit is adapted to measure the several temperature values at the several locations along the length of the blood vessel such that the temperature profile is generated and to provide the first temperature value and/or the second temperature value based on these measured several temperature values. Thus, the temperature values determining unit can be adapted to provide a spatially distributed temperature sensing for measuring several temperature values at several locations and to provide the first and second temperature values based on these measured several temperature values forming the temperature profile. Since the first and second locations are determined based on the measured temperature profile, the blood flow determination can be less sensitive to involuntary movements of the temperature values determining unit and the blood vessel relative to each other. The temperature values determining unit can be adapted to measure more than 10, preferentially more than 50, and further preferred more than 100 temperature values at a corresponding number of point locations along the length of the blood vessel. Preferentially, the optical fiber and the swept-wavelength interferometry are used for measuring the several temperature values at the several locations. It should be noted that the expression "A and/or B" preferentially covers following options: a) only A, b) only B, or c) A and B.

The temperature values determining unit can be adapted to provide a user interface, particularly a graphical user interface, for allowing a user to indicate point locations or sections along the length of the blood vessel as the first and second locations, respectively, and to determine the first temperature value and the second temperature value, respectively, based on the temperature values measured for these indicated point locations or sections. For instance, if the user has indicated a section for which several temperature values have been measured at different point locations within the section, the temperature values determining unit can spatially average these temperature values for providing a temperature value for this indicated section. The temperature values determining unit can also be adapted to determine the first location and/or the second location based on the measured several temperature values and to determine the first temperature value and/or the second temperature value, respectively, based on the determined first location and/or the determined second location, respectively, and the temperature values measured for these locations. For instance, the temperature values determining unit can be adapted to determine a section along the length of the blood vessel within which a spatial variation of the measured several temperature values is minimal or smaller than a predefined spatial variation threshold, in order to determine the second location. The first location and/or the second location can also be predefined with respect to an infusion location at which the fluid is infused into the blood vessel. For instance, the first location can be the infusion location and the second location can be a location having a predefined distance to the infusion location along the length of the blood vessel.

In an embodiment the temperature values determining unit can be adapted to temporally average the measured temperature values. Thus, temperatures can be measured over time and temporally averaged. The temporally averaged measured temperature values, i.e. the temporally averaged temperature profile formed by the temporally averaged measured temperature values, can then be used for determining the first and second temperature values. The temporal averaging can lead to an improved quality of the temperature values and hence to a further improved accuracy of determining the blood flow.

In a preferred embodiment the fluid infusion unit comprises a tube with a tube opening, wherein the tube is adapted to guide the fluid into the blood vessel such that the fluid leaves the tube through the tube opening, wherein the temperature values determining unit is adapted to determine a) the first temperature value such that it is indicative of the temperature within the tube and/or at the tube opening outside of the tube, wherein the first location is within the tube and/or at the location of the tube opening, respectively, and b) the second temperature value such that it is indicative of the temperature at a location which is distal from the tube opening location and which is the second location.

Moreover, the temperature values determining unit can be adapted to measure several temperature values at several locations along the length of the blood vessel, which are distal from the tube opening location, wherein the system can further comprise an assessment unit for determining a quality value being indicative of a degree of mixing of the fluid and the blood based on these measured several temperature values. In particular, the assessment unit can be adapted to determine a quality value indicating a sufficient degree of mixing, if a spatial variation of the temperature values is smaller than a predefined spatial threshold. Thus, an indicator can be given for the degree of mixing and hence for the accuracy of the determination of the blood flow. The assessment unit can be integrated with one or several other units like the temperature values determining unit, the locations determination unit, et cetera, or it can be a separate unit.

The fluid infusion unit can be adapted to control the temperature of the fluid depending on the first temperature value and/or the second temperature value. In particular, the fluid infusion unit can be adapted to control the temperature of the fluid such that a difference between a) the absolute temperature of the fluid within the blood vessel and/or the absolute temperature of the mixture within the blood vessel and b) the absolute temperature of the blood within the blood vessel is relatively large, in particular larger than a predefined temperature threshold. This can lead to a corresponding relatively large signal-to-noise ratio and hence to a further improved accuracy of the determination of the blood flow.

The fluid infusion unit can be adapted to infuse the fluid into the blood vessel with a constant infusion rate or with a varying infusion rate. For instance, the fluid infusion unit can be adapted to infuse the fluid into the blood vessel only with a constant infusion rate, or the fluid infusion unit can be adapted to be operable with a constant infusion rate or with a varying infusion rate, i.e. the same fluid infusion unit may be used with a constant infusion rate and a varying infusion rate. In particular, the blood flow determining unit can be adapted to determine the blood flow over time, while the infusion rate is varied, wherein the system can further comprise an assessment unit for determining a quality value being indicative of the quality of determining the blood flow based on a variation of the blood flow determined over time. In particular, by comparing the variation of the infusion rate and the variation of the determined blood flow it can be determined whether the determination of the blood flow is adversely affected by, for instance, a vasodilatory response from a microcirculation. Also this assessment unit can be integrated with one or several other units like the temperature values determining unit, the locations determination unit, et cetera, or it can be a separate unit.

In a further aspect of the present invention a method for determining blood flow is presented, wherein the method comprises:

simultaneously measuring several temperature values at several locations along the length of the blood vessel such that a temperature profile along the length of the blood vessel is determined and determining, based on these measured several temperature values, a first temperature value at a first location along the length of the blood vessel and a second temperature value at a second location along the length of the blood vessel, while a fluid is continuously infused into the blood vessel with an infusion rate by using a fluid infusion unit, such that the first temperature value is indicative of the temperature of the fluid and the second temperature value is indicative of the temperature of a mixture of the fluid and the blood, determining the blood flow based on the determined first and second temperature values and the infusion rate by using a blood flow determining unit.

In another aspect of the present invention a computer program for determining blood flow within a blood vessel is presented, wherein the computer program comprises program code means for causing a system for determining blood flow within a blood vessel as defined in the claims to carry out the method for determining blood flow within a blood vessel as defined in the claims, when the computer program is run on the system.

It shall be understood that the system of the claims, the method of the claims and the computer program of the claims have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
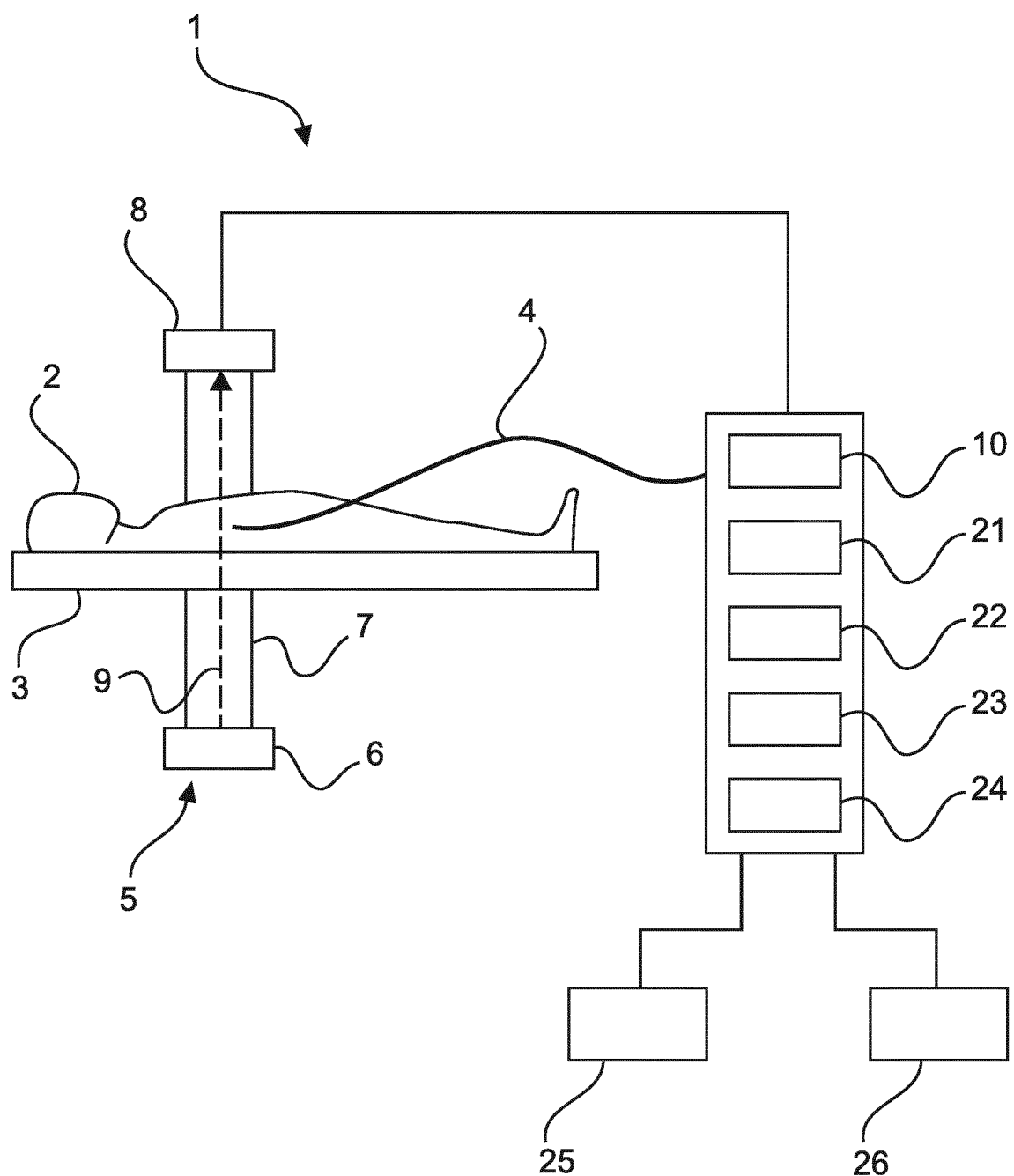
FIG. 1 shows schematically and exemplarily an embodiment of a system for determining blood flow within a blood vessel.
Figure 2:
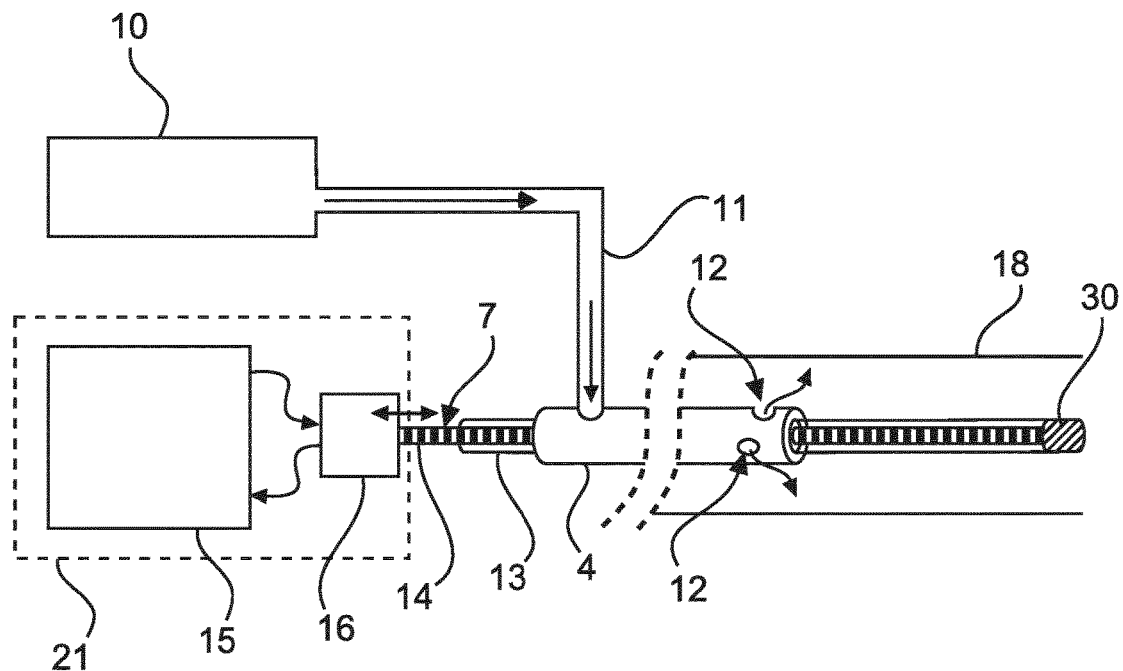
FIGS. 2 to 4 show schematically and exemplarily details of the embodiment of the system shown in FIG. 1.
Figure 3:
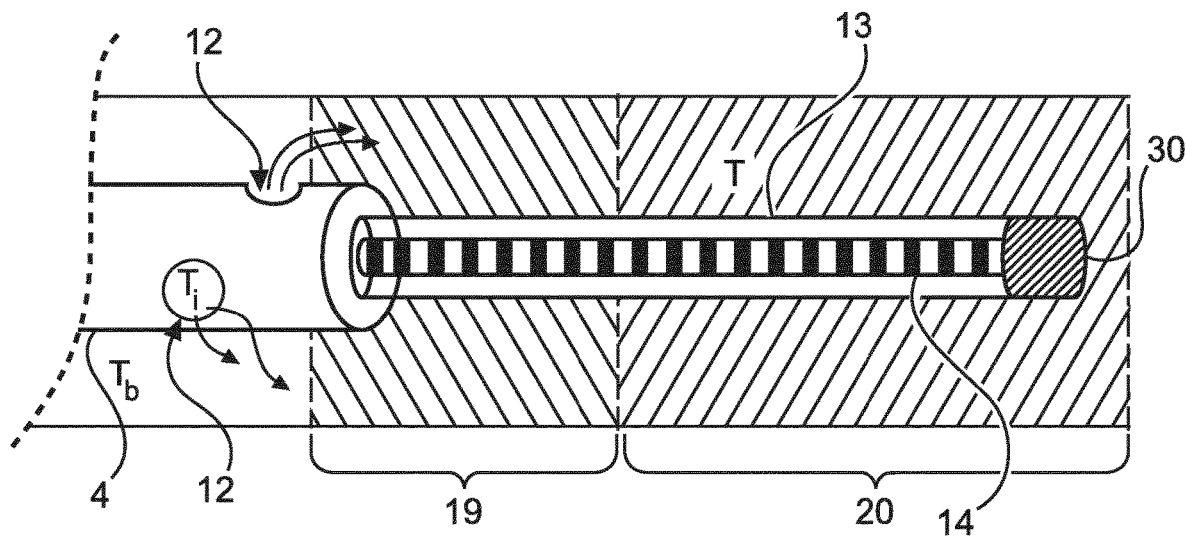

FIG. 1 shows schematically and exemplarily an embodiment of a system 1 for determining blood flow within a blood vessel of a patient 2 lying on a patient table 3. FIGS. 2 and 3 schematically and exemplarily show some details of this system 1. The system 1 comprises an infusion pump 10 which is connected to a tube 4 being, in this embodiment, an infusion catheter via a fluid connection 11. The infusion pump 10, the fluid connection 11 and the tube 4 can be regarded as forming a fluid infusion unit which is adapted to continuously infuse a fluid into the blood vessel 18 with a constant or varying infusion rate such that a mixture of the fluid and the blood is generated within the blood vessel 18. The fluid leaves the tube 4 through tube openings 12, whereafter the fluid is mixed with the blood in a mixing zone 19, wherein in this embodiment in a mixed zone 20 the fluid and the blood have been mixed completely.

The system 1 further comprises an optical signals unit 21 for generating, detecting and processing optical signals, which is connected to an optical fiber 14. The optical signals unit 21 generates optical signals which are provided to the optical fiber 14, receives and detects optical signals from the optical fiber 14 and processes the received and detected optical signals, in order to determine temperature values being indicative of the temperatures at several locations along the length of the optical fiber 14. The optical signals unit 21 includes a first part 15 which comprises an optical source and an optical detector for generating and detecting the optical signals and a processor for processing the detected optical signals, and a second part 16 being an optical circulator for coupling the generated optical signals into the optical fiber 14 and for receiving optical signals from the optical fiber 14. The optical signals unit 21 and the optical fiber 14 are adapted such that they allow for a simultaneous determination of temperature values being indicative of temperatures at locations along the length of the optical fiber 14. These temperature values include a first temperature value at a first location along the length of the blood vessel and a second temperature value at a second location along the length of the blood vessel such that the first temperature value is indicative of the temperature of the fluid and the second temperature value is indicative of the temperature of the mixture. The optical fiber 14 and the optical signals unit 21 can therefore be regarded as forming a temperature values determining unit for simultaneously determining the first and second temperature values at the first and second locations, respectively, along the length of the blood vessel 18. In this embodiment the temperature values determining unit is adapted to determine the first temperature value such that it is indicative of the temperature at the tube openings 12 within or outside of the tube 4 and the second temperature value such that it is indicative of the temperature at a location within the mixed zone 20 being the second location. The temperature values determining unit can be adapted to determine the location of the mixed zone 20 based on the spatially distributed temperature sensing, i.e. based on the several temperature values determined at the several locations along the length of the blood vessel. In particular, the temperature values determining unit can be adapted to determine the section along the length of the blood vessel, within which the spatial variation of the temperature values is minimal, as the mixed zone. For instance, a window with a predefined width can be arranged along the length of the blood vessel such that the spatial variation of the temperature values within the window is minimal. For this determination of the location of the mixed zone 20 temporally averaged temperature values are preferentially used.

The system 1 further comprises a longish guiding element 13 being, in this embodiment, a guidewire for guiding the tube 4 into the blood vessel 18, wherein the optical fiber 14 is integrated with the guiding element 13, i.e. the guiding element 13 and the optical fiber 14 are attached to each other. In this embodiment the optical fiber 14 is arranged within the guiding element 13 along the longitudinal axis of the guiding element 13.

The system 1 further comprises a blood flow determining unit 22 for determining the blood flow, i.e. the volumetric blood flow which might be defined as volumetric blood flow rate, based on the measured first and second temperature values and the infusion rate. In this embodiment the temperature values determining unit 14, 21 is adapted to determine relative first and second temperature values being indicative of respective relative temperatures with respect to the blood temperature, i.e. the temperature of the blood if the fluid is not present. The blood flow determining unit 22 can be adapted to determine the blood flow $Q_b$ in accordance with following equation:

$$Q_b = \frac{\rho_i c_i}{\rho_b c_b} \left[ \frac{T_b - T_i}{T_b - T} \right] Q_i,$$

wherein $\rho_i$ is the known density of the fluid which may also be regarded as being an indicator fluid, $\rho_b$ is the known density of the blood, $c_i$ is the known specific heat of the fluid, $c_b$ is the known specific heat of the blood, $T_b - T_i$ is the relative temperature of the fluid, i.e. in this embodiment the first temperature value, $T_b - T$ is the relative temperature of the mixture, i.e. in this embodiment the second temperature value, and $Q_i$ is the infusion rate of infusing the fluid into the blood vessel, wherein this infusion rate might be constant.

The temperature values determining unit 14, 21 is not adapted to determine only two temperature values at a first location and at a second location, but to determine several temperature values being indicative of temperatures at many different locations along the length of the optical fiber 14. In particular, the temperature values determining unit 14, 21 is adapted to determine several temperature values being indicative of temperatures at several locations along the length of the optical fiber 14 within the mixing zone 19 and within the mixed zone 20. The system 1 further comprises an assessment unit 24 for determining a quality value being indicative of a degree of mixing of the fluid and the blood within the mixed zone 20 based on the determined several temperature values in the mixing zone 19 and/or in the mixed zone 20. In particular, the assessment unit 24 is adapted to determine a quality value indicating a sufficient degree of mixing, if a spatial variation of these temperature values is smaller than a predefined spatial threshold, wherein these temperature values are preferentially temporally averaged temperature values.

For instance, the value of quality of mixing can be quantified by calculating a measure for how the time-averaged temperature spatially varies in the mixed zone, in particular, by calculating the mean squared error from the temporal average temperature values in the mixed zone in accordance with following equation:

$$MSE = \frac{1}{n} \sum_{j=1}^{n} \left( T_j - \frac{1}{n} \sum_{j=1}^{n} T_j \right)^2$$

wherein MSE denotes the quality value indicating the degree of mixing, n denotes the number of temperature values within the mixed zone 20, and $T_j$ the temporally averaged temperature values within the mixed zone 20.

The optical signals unit 21 is adapted to use swept-wavelength interferometry for measuring temperature changes in the optical fiber 14. In particular, the first part 15 of the optical signals unit 21 includes a tunable laser source, wherein laser light emitted by the tunable laser source is coupled into the optical fiber and based on perturbations in a backscatter pattern detected by a light detector of the first part 15 of the optical signals unit 21 small differences in local temperatures can be determined. By using this technique temperature profiles along the optical fiber 14 can be determined with a high temporal resolution and a high spatial resolution. For more details regarding this swept-wavelength interferometry technique reference is made to the Article "High Resolution Distributed Strain or Temperature Measurements in Single- and Multi-mode Fiber Using Swept-Wavelength Interferometry" by S. T. Kreger et al., Optical Fiber Sensors, Optical Society of America (2006) and WO 2012/164481 A1, which are herewith incorporated by reference. In this embodiment the optical fiber 14 is an optical fiber with an inscribed Bragg grating pattern. However, in another embodiment also another optical fiber can be used like a standard optical glass fiber where backscatter characteristics are caused by intrinsic density changes in the glass, i.e. by Rayleigh scattering.

In the example described above with reference to FIGS. 1 to 3 the blood vessel 18 is a coronary artery. Before the fluid is infused into the coronary artery via the tube 4, the first part 15 of the optical signals unit 21 preferentially carries out a baseline measurement for determining a reference state of the optical fiber 14 at the blood temperature $T_b$. The temperature values, which are determined while the fluid is infused into the blood vessel 18, will then automatically be relative temperature values being indicative of relative temperatures which are relative with respect to the blood temperature $T_b$. The baseline measurement might be carried out as described in the above mentioned article by S. T. Kreger et al. and the above mentioned WO 2012/164481 A1.

The fluid, which might also be regarded as being an indicator fluid, is preferentially a saline solution having a temperature being smaller than the temperature of the blood. Preferentially, the saline solution has a temperature being equal to the room temperature. The infusion pump 10 is preferentially adapted to provide a steady flow of the saline solution through the tube 4 into the coronary artery 18, which results in a temperature drop at the tip of the tube 4 ($\Delta T_i = T_b - T_i$).

The tube 4, i.e. in this embodiment the catheter, comprises the tube openings 12 at its side, in order to enhance mixing. The mixing takes place in the mixing zone 19 such that distal to the mixing zone 19, i.e. in the mixed zone 20, the blood and the fluid are completely mixed, which means that at a second location within this mixed zone 20 the temperature drop relative to the reference measurement, i.e. the relative second temperature value $\Delta T = T_b - T$, can be related to the blood flow in accordance with the above mentioned equation. Since the temperature measurement is spatially distributed, the quality of mixing can be evaluated simultaneously by determining the temperature profile in the mixed zone 20 and/or in the mixing zone 19. Large spatial and/or temporal temperature changes are an indicator that mixing is not complete.

Although in the embodiments described above with reference to FIGS. 1 to 3 the optical fiber 14 is arranged within the guiding element 13, in other embodiments the optical fiber 14 can also be integrated with the guiding element 13 in another way. In particular, the optical fiber 14 can be located at the outside of the guiding element 13, in order to enhance the thermal contact between the optical fiber 14 and the surrounding blood, indicator fluid and mixture of the blood and the indicator fluid. The optical fiber can be integrated in a small slit on the outside of the guiding element. The optical fiber can be integrated along the longitudinal axis of the optical fiber. However, the optical fiber can also be wound around the guiding element. The latter configuration can also be used to give information about the temperature distribution on the parameter of the guiding element, wherein this perimetric temperature distribution can be used to provide additional information concerning the mixing of the blood and the indicator fluid.

The infusion pump 10 is preferentially adapted to control the temperature of the fluid outside the patient 2, especially within the infusion pump 10, depending on the first temperature value and/or the second temperature value. In particular, the infusion pump 10 can be adapted to control fluid temperature outside the patient 2 and hence the first temperature value $\Delta T_i$ by using a feedback mechanism, wherein the temperature of the indicator fluid outside the patient 2 is adapted depending on the first temperature value $\Delta T_i$, which is determined by using the optical fiber 14, such that the first temperature value $\Delta T_i$ has a desired value. This can allow for an increased signal-to-noise ratio by decreasing the temperature of the indicator fluid outside the patient 2, especially within the infusion pump 10, in a controlled and safe way. In particular, the temperature of the indicator fluid outside the patient 2 can be controlled such that the relative first temperature value $\Delta T_i$ has a desired value which is known to provide a sufficient signal-to-noise ratio.

If in an embodiment the temperature of the indicator fluid outside the patient is controlled depending on the second temperature value $\Delta T_i$ a compensation of low $|\Delta T|$ due to high flow rates can be provided. Moreover, also this enables increasing the signal-to-noise ratio in a safe and a controlled way.

In order to assess the quality of the determination of the blood flow, the infusion rate can be varied and the blood flow can be determined over time during the variation of the infusion rate. In particular, the blood flow determining unit 22 can be adapted to determine the blood flow over time, while the infusion pump 10 varies the infusion rate, wherein the system 1 can further comprise an assessment unit 24 for determining a quality value being indicative of the quality of determining the blood flow based on a variation of the blood flow determined over time. By changing, particularly by sweeping, the infusion rate $Q_i$ during the determination of the blood flow, the effect of the infusion of the indicator fluid on the original blood flow, i.e. the applicability of the above mentioned equation, can be evaluated. In this way it can be determined if, for example, the injection itself increases the perfusion pressure or if there is a vasodilatory response from the microcirculation due to an insufficient administration of vasoactive drugs. This quality assessment is possible because of the distributed temperature sensing which leads to a simultaneous determination of the first and second temperature values $\Delta T$ and $\Delta T_i$. The changing, in particular the sweeping, of the infusion rate $Q_i$ is preferentially performed in a quasi-steady way to keep the continuous nature of the blood flow determination.

In particular, the assessment unit 24 can be adapted to determine the quality value by determining how the blood flow $Q_b$ changes, when the infusion rate $Q_i$ is changed. For instance, the quality value can be or depend on $dQ_b/dQ_i$, wherein $dQ_b$ denotes a change of the blood flow $Q_b$ and $dQ_i$ denotes a change of the infusion rate. Since the determined blood value $Q_b$ should be independent of the infusion rate $Q_i$, a smaller quotient $dQ_b/dQ_i$ indicates a higher quality of the determination of the blood flow.

The system 1 further comprises a fluoroscopy device 5 comprising a radiation source 6 for emitting x-rays 9 and a radiation detector 8 for detecting the x-rays 9 after having traversed the patient 2, in order to generate an x-ray image showing the inside of the patient 2. The system 1 further comprises a display 26 for showing the generated x-ray image of the patient 2. The x-ray image can be generated at different points in time, in order to assist a user like a physician in navigating the tube 4 within the patient 2. The radiation source 6 and the radiation detector 8 are mounted to opposing ends of a C-arm 7.

The first part 15 of the optical signals unit 21 can also be adapted to determine the different locations, for which the several temperature values are determined, based on the optical signals received from the optical fiber 14. In particular, the optical fiber 14 can be an optical shape sensing fiber which allows determining the shape of different segments of the optical fiber and hence the entire shape of the optical fiber, wherein this shape information can be used to determine the locations along the length of the optical fiber, for which the temperature values are determined. Thus, the exact locations, especially the first and second locations for which the first and second temperature values are determined, can be derived by optical shape sensing, without using the fluoroscopy device 5. Thus, in an embodiment the system 1 does not comprise the fluoroscopy device 5 and is adapted to show the position of the optical fiber and hence of the guiding element within the patient 2 on the display 26 by using optical shape sensing. In particular, the optical shape sensing localization technique can be registered with a pre-acquired anatomical image of the patient like a pre-acquired computed tomography image or magnetic resonance image and the determined position of the optical fiber and hence of the guiding element can be shown relative to the pre-acquired anatomical image of the patient on the display 26, in order to assist the user while navigating the guiding element within the patient. The optical shape sensing fiber can be a multicore optical fiber as disclosed in, for instance, WO 2012/121584 A2 which is herewith incorporated by reference.

Figure 4:
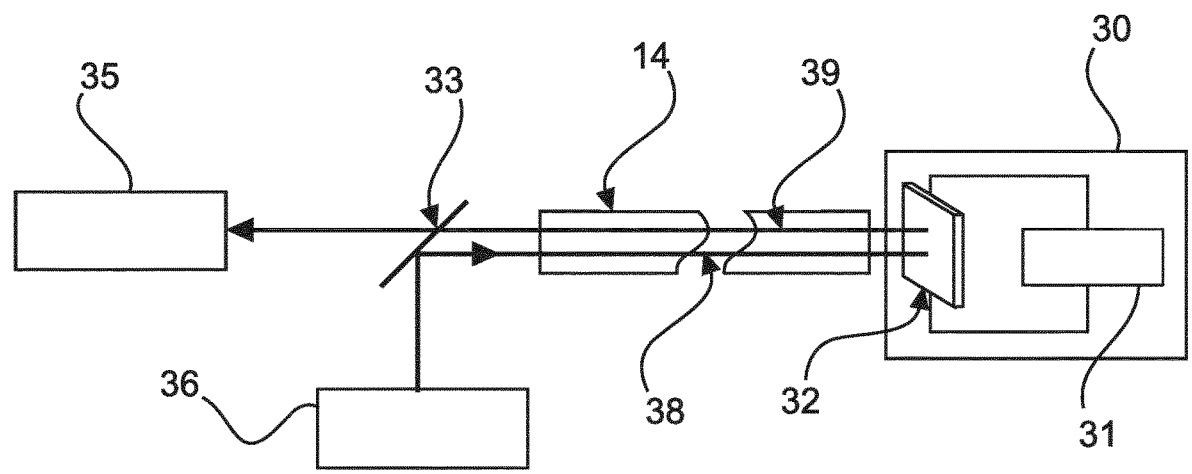

As schematically and exemplarily illustrated in FIGS. 2 to 4, the guiding element 13 comprises at its distal tip a sensing device 30 with a sensor 31 for generating a sensing signal depending on a property to be sensed within the blood vessel and with a power generation and signal transmission unit 32 for powering the sensor 31 by using light 38 received from the optical fiber 14 and for transmitting the sensing signal via the optical fiber 14 to the optical signals unit 21 outside of the blood vessel 18. In particular, the sensor 31 is adapted to generate a pressure sensing signal being indicative of the pressure in the blood, wherein the system 1 comprise a resistance determination unit 23 for determining the resistance based on the pressure indicated by the pressure sensing signal and the determined blood flow. The determined resistance can be shown on the display 26. Thus, by using the sensing device 30 with the sensor 31 added to the tip of the guiding element 13 and there connected to the optical fiber 14 pressure sensing can be combined with volumetric flow determination, thereby enabling an interrogation of a microvascular disease like a coronary stenosis based on this determined resistance.

In particular, the first part 15 of the optical signals unit 21 can comprise a further optical source 36 for providing powering light 38 to be transmitted to the power generation and signal transmission unit 32 and a further optical detector 35 for receiving optical data signals 39 from the power generation and signal transmission unit 32 via the optical fiber 14. The first part 15 or the second part 16 can further comprise a dichroic mirror 33 for separating the powering light 38 to be coupled into the optical fiber 14 from the optical data signals 39 sent by the power generation and signal transmission unit 32. In an embodiment the further optical source 36 can be a blue-ray laser emitting powering light 38 having a wavelength of 405 nm, the power generation and signal transmission unit 32 can be a blue light-emitting diode (LED) generating optical data signals 39 having a wavelength of 450 nm, and the further optical detector 35 can be a photodiode detecting the optical data signals 39 having the wavelength of 450 nm. Thus, the same LED 32 can be used for powering the sensor 31, when illuminated by the powering light, and for transmitting the sensing signal. Instead of the wavelengths of 405 nm and 450 nm also other wavelengths can be used for the powering light and the optical data signals. For more details regarding the optical powering and data transmission via an optical fiber reference is made to, for instance, US 2015/0335231 A1 which is herewith incorporated by reference.

It should be noted that for clarity reasons FIG. 4 only illustrates the powering and data transmission components, although the system comprises further components, in particular as described above with respect to FIGS. 2 and 3. The optical fiber 14 can comprise, for instance, a single mode core for the sensing of the temperature distribution and for the determination of the locations and a multimode cladding for the power and data path.

The tip of the guiding element 13 with the sensing device 30 can be moved to different locations within the blood vessel 18 to determine a pressure gradient $\Delta P$, wherein the resistance determination unit 23 can be adapted to determine the resistance R in accordance with the equation $R=\Delta P/Q_b$. For instance, at two different locations the pressure can be measured, in order to determine the pressure gradient $\Delta P$ and hence the resistance R. It is also possible that the guiding element 13 comprises at least two pressure sensors at at least two different locations along the length of the guiding element 13 and thus along the length of the blood vessel, in order to allow for a determination of the pressure gradient $\Delta P$ without moving the guiding element 13.

Alternatively or in addition, one or several other sensors can be attached to, for instance, the tip of the guiding element and connected to the optical fiber, in order to power also these sensors by using the light received from the optical fiber and for transmitting sensor signals generated by the sensors via the optical fiber to the outside of the patient.

The system 1 further comprises an input unit 25 like a keyboard, a computer mouse, a touchpad, et cetera, in order to allow a user to, for instance, input commands like start commands for starting a blood flow determination procedure or other data into the system 1.

Figure 5:
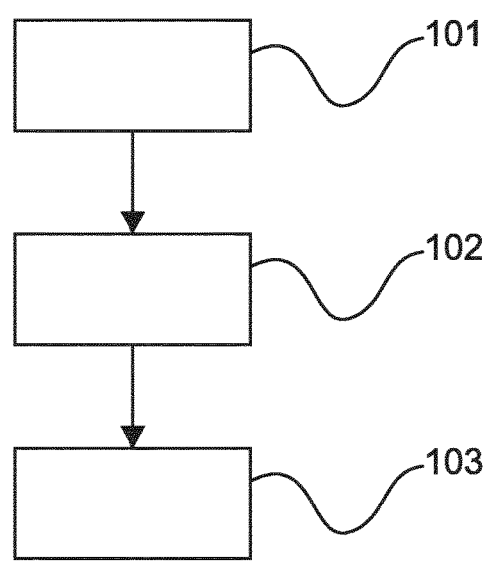
FIG. 5 shows a flowchart exemplarily illustrating an embodiment of a method for determining blood flow within a blood vessel.

In the following an embodiment of a method for determining blood flow within a blood vessel will exemplarily be described with reference to a flowchart shown in FIG. 5.

While the indicator fluid is continuously infused into the blood vessel 18 by using the fluid infusion unit 4, 10, 11, in step 101 the first temperature value at the first location along the length of the blood vessel 18 and the second temperature value at the second location along the length of the blood vessel 18 are simultaneously determined by the temperature values determining unit 14, 21 such that the first temperature value is indicative of the temperature of the fluid and the second temperature value is indicative of the temperature of a mixture of the fluid and the blood. In step 102 the blood flow is determined based on the measured first and second temperature values and the infusion rate, with which the indicator fluid is infused into the blood vessel 18, by using the blood flow determining unit 22. In step 103 the determined blood flow is shown on the display 26.

The procedure of determining the blood flow described above with reference to FIGS. 1 to 5 is preferentially performed when the coronary circulation is in hyperemia, i.e., for instance, when corresponding vasoactive drugs have been induced. The mixing zone 19 just distal to the tube 4 may have a size of about 5 to 8 cm, depending on the actual flow in the blood vessel. The second temperature value is preferentially determined for a second location being distal to this mixing zone 19, wherein it is assumed that distal of the mixing zone 19, i.e. within the mixed zone 20, the degree of mixing of the blood and the indicator fluid is sufficient for accurately determining the blood flow based on the determined temperature values.

The system 1 is adapted to determine the blood flow, i.e. the volumetric blood flow, which is not the blood velocity or a spatial derivative of the blood velocity. The continuous infusion thermodilution technique disclosed in the above mentioned article by M. van 't Veer et al. also allows for a determination of an intravascular blood flow, i.e. of an intravascular volumetric blood flow. However, as described above, a guidewire equipped with a single temperature sensor is used to measure at at least two locations along the length of the blood vessel, i.e. at the tip of the tube, at which the indicator fluid leaves the tube, and at a certain distance from the tube, at which the indicator fluid has been mixed completely with the blood. This requires repositioning of the guidewire during the procedure. In contrast, the system 1 described above with reference to FIGS. 1 to 4 allows for a measurement of a temperature distribution along the optical fiber and hence along the guiding element with high temporal resolution and high spatial resolution, especially by using swept-wavelength interferometry, without requiring a repositioning of the optical fiber and hence the guiding element. This allows for a simplified procedure and the distributed temperature measurement can also be used to monitor the quality of the volumetric blood flow determination.

Compared to the known continuous thermodilution technique using the single point temperature device, the system described above with reference to FIGS. 1 to 4 has the advantage that the temperature of both, the mixture distal to the catheter, i.e. to the tube guiding the indicator fluid into the blood vessel, and the indicator fluid at the end of the catheter, can be obtained simultaneously. This reduces the number of steps to be carried out while performing the procedure, because a pullback of the guidewire into the catheter is not required. Moreover, this simultaneous determination of the different temperatures is more accurate, because there is less time between the different temperature measurements. Moreover, since the temperature measurement is spatially distributed, the temperatures in the mixing zone and/or in the mixed zone can be measured simultaneously. This allows for providing an indicator of the quality of the mixing and hence allows for an accurate flow assessment. Furthermore, by using the optical fiber for measuring the temperature distribution, the blood flow determination procedure is insensitive to electromagnetic interferences and compatible with magnetic resonance guided interventions.

Although in above described embodiments the optical fiber comprises an inscribed Bragg grating pattern, in other embodiments another optical fiber can be used which allows for a temperature measurement based on Rayleigh scattering. Rayleigh scattering originates from a random distribution of small refractive index changes in the optical fiber, wherein these variations can be viewed as random Bragg periods. By determining the temperature based on Rayleigh scattering optical fibers can be used, which are easy to manufacture and which are therefore more cost effective.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of the blood flow, the determination of a resistance, the determination of a quality value, et cetera performed by one or several units or devices can also be performed by any other number of units or devices. These operations and/or the control of the system for determining blood flow within a blood vessel in accordance with the method for determining blood flow within the blood vessel can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for determining blood flow within a blood vessel. A fluid infusion unit continuously infuses a fluid into the blood vessel, and a temperature values determining unit determines simultaneously a first temperature value at a first location and a second temperature value at a second location such that the first temperature value is indicative of the temperature of the fluid and the second temperature value is indicative of the temperature of a mixture of the fluid and the blood. The blood flow is determined based on the measured first and second temperature values and the infusion rate. This kind of determining the blood flow leads to an increased accuracy and is less cumbersome than known techniques requiring a movement of a temperature sensor for measuring temperatures at different locations.

The invention claimed is:

1. An apparatus, comprising:
a guidewire configured to be positioned within a blood vessel, wherein the blood vessel comprises a mixture of blood and a fluid infused into the blood vessel at an infusion rate, wherein the guidewire comprises a first temperature sensing portion configured to measure a first temperature value at a first location within the blood vessel and a second temperature sensing portion configured to measure a second temperature value at a second location within the blood vessel, wherein the first temperature sensing portion and the second temperature sensing portion are arranged along a length of the guidewire such that the first temperature value and the second temperature value are measured without movement of the guidewire through the blood vessel; and a system configured to determine a blood flow within the blood vessel based on a relationship including the infusion rate and a plurality of temperature values associated with the fluid, wherein all of the plurality of temperature values associated with the fluid are measured after a start of infusion of the fluid into the blood vessel, wherein the plurality of temperature values associated with the fluid comprise the first temperature value and the second temperature value.

2. The apparatus of claim 1, wherein the guidewire further comprises a sensor configured to generate a sensing signal representative of a property within the blood vessel.

3. The apparatus of claim 2,
wherein the sensor comprises a pressure sensor, and
wherein the sensing signal comprises a pressure sensing signal representative of a pressure within the blood vessel.

4. The apparatus of claim 1,
further comprising a catheter configured to be positioned within the blood vessel,
wherein the catheter comprises an opening configured to deliver the fluid into the blood vessel.

5. The apparatus of claim 4, wherein the guidewire is configured to extend distal of the catheter such that the first temperature sensing portion and the second temperature sensing portion are distal of the catheter.

6. The apparatus of claim 4, further comprising an infusion pump coupled to the catheter and configured to provide the fluid.

7. The apparatus of claim 1, wherein the first temperature sensing portion and the second temperature sensing portion are configured to measure the first temperature value and the second temperature value simultaneously.

8. The apparatus of claim 1,
wherein the guidewire comprises an optical fiber, and
wherein the optical fiber comprises the first temperature sensing portion and the second temperature sensing portion.

9. A method, comprising:
measuring a first temperature value at a first location within a blood vessel using a first temperature sensing portion of a guidewire positioned within the blood vessel, wherein the blood vessel comprises a mixture of blood and a fluid infused into the blood vessel at an infusion rate;

measuring a second temperature value at a second location within the blood vessel using a second temperature sensing portion of the guidewire, wherein the first temperature sensing portion and the second temperature sensing portion are arranged along a length of the guidewire such that the first temperature value and the second temperature value are measured without movement of the guidewire through the blood vessel; and determining a blood flow within the blood vessel based on a relationship including the infusion rate and a plurality of temperature values associated with the fluid, wherein all of the plurality of temperature values associated with the fluid are measured after a start of infusion of the fluid into the blood vessel, wherein the plurality of temperature values associated with the fluid comprise the first temperature value the second temperature value.

10. A non-transitory computer-readable medium comprising program code configured to cause an apparatus to carry out the method of claim 9.

* * * * *